United States Patent [19]

Hashizume et al.

[11] Patent Number: 5,763,648

[45] Date of Patent: Jun. 9, 1998

[54] PROCESS FOR PRODUCING AN AROMATIC CARBOXYLIC ACID

[75] Inventors: Hiroshi Hashizume, Tokyo; Takashi Komaya; Katsunori Fukuda, both of Kitakyushu, all of Japan

[73] Assignee: Mitsubishi Chemical Corporation, Tokyo, Japan

[21] Appl. No.: 797,122

[22] Filed: Feb. 10, 1997

[30] Foreign Application Priority Data

Feb. 13, 1996 [JP] Japan .................................. 8-025388

[51] Int. Cl.$^6$ ................................................. C07C 5/265
[52] U.S. Cl. ................................................. 562/414
[58] Field of Search ........................... 562/414, 416

[56] References Cited

U.S. PATENT DOCUMENTS 4,593,122  6/1986  Hashizume et al. .
4,827,025  5/1989  Shiraki et al. .

FOREIGN PATENT DOCUMENTS 0 673 910  9/1995  European Pat. Off. .
45-36732  11/1970  Japan .

*Primary Examiner*—Samuel Barts
*Attorney, Agent, or Firm*—Oblon, Spivak, McClelland, Maier & Neustadt, P.C.

[57] ABSTRACT

A process for producing an aromatic carboxylic acid, which comprises oxidizing an alkylaromatic hydrocarbon with a molecular oxygen-containing gas in a liquid phase in an acetic acid solvent in the presence of catalyst components comprising cobalt, manganese and bromine, wherein (1) the reaction temperature is from 140° to 180° C., (2) the cobalt component is in an amount of from 400 to 3.000 ppm by weight to the acetic acid solvent, as calculated as cobalt metal, (3) the manganese component is in an amount of from 0.001 to 0.4 time in the atomic ratio to cobalt, (4) the bromine component is in an amount of from 0.1 to 5.0 times in the atomic ratio to cobalt, (5) a part of an oxidation exhaust gas obtained by removing condensable components by condensation from a gas withdrawn from the reactor, is recycled to a liquid phase in the reactor, and (6) the reaction pressure is adjusted to a level which is higher than the pressure for a case where air is used as the molecular oxygen-containing gas and no recycling of the oxidation exhaust gas is carried out.

18 Claims, 1 Drawing Sheet

PROCESS FOR PRODUCING AN AROMATIC CARBOXYLIC ACID

BACKGROUND OF THE INVENTION

1. Field of the Invention

The present invention relates to a process for producing an aromatic carboxylic acid. Particularly, it relates to a process for producing an aromatic carboxylic acid of a high quality by a liquid phase oxidation reaction of an alkylaromatic hydrocarbon, while substantially preventing a combustion loss of acetic acid as the solvent for the reaction.

2. Discussion of Background

As a process for producing an aromatic carboxylic acid such as terephthalic acid, a process is industrially most common wherein an alkylaromatic hydrocarbon such as p-xylene is subjected to a liquid phase oxidation reaction with molecular oxygen in an acetic acid solvent in the presence of a catalyst containing cobalt, manganese and bromine. When terephthalic acid is produced by subjecting p-xylene to a liquid phase oxidation reaction by this process, 4-carboxybenzaldehyde (hereinafter referred to simply as "4CBA") as one of intermediates in the process or many impurities formed by side-reactions, will be included in the terephthalic acid. Accordingly, the quality of the terephthalic acid product, particularly the light transmissivity (hereinafter sometimes referred to simply as "transmissivity") at 340 nm of its alkaline aqueous solution, will change. Therefore, in the industrial production of high purity terephthalic acid, the quality of the product is judged and controlled usually by using the light transmissivity and the 4CBA content of the terephthalic acid product, as indices.

Usually, the quality of terephthalic acid can be adjusted by selecting oxidation reaction conditions such as the reaction temperature, the amount of the catalyst and the resident time in the oxidation reactor. However, in order to produce terephthalic acid of a high quality having a low content of 4CBA and high transmissivity, it is usually required to select severe conditions for the oxidation reaction. Accordingly, the acetic acid solvent is likely to undergo combustion or decomposition, and its loss tends to be substantial, thus leading to a problem that the production cost of terephthalic acid increases.

If the reaction temperature for the oxidation reaction is lowered to prevent the loss of acetic acid due to combustion or decomposition, the reaction activities will also decrease substantially, whereby the resulting terephthalic acid will be of a low quality with a low transmissivity and a high content of 4CBA. Also in literatures, there has been no report on a reaction carried out for industrial production within a temperature range of not higher than 180° C. except for a special case where an oxidation reaction system employing a reaction accelerator such as a co-oxidizing agent, is used. Even if a temperature range of not higher than 180° C. can be set, it will be necessary to set such a condition that the concentration of the catalyst is extremely high, and there will be substantial disadvantages with respect to the production cost and the quality of terephthalic acid.

In the process for producing an aromatic carboxylic acid by a liquid phase oxidation reaction of an alkylaromatic hydrocarbon as described above, the following improvements have been proposed in recent years.

① JP-B-5-32381 (U.S. Pat. No. 4,593,122) discloses a process for producing terephthalic acid excellent in the transmissivity, by carrying out the oxidation reaction while increasing the oxygen partial pressure in the gas phase of the reaction system by recycling a part of the oxidation exhaust gas to a liquid phase in the reactor. By this process, improvements are observed in the transmissivity of terephthalic acid and the polymerized color. However, there is no substantial difference from the conventional process with respect to the amount of combustion or decomposition of the acetic acid solvent for the production of terephthalic acid containing the equal amount of 4CBA.

② JP-B-7-88211 (U.S. Pat. No. 4,827,025) discloses a process wherein a part of the oxidation exhaust gas is recycled to the gas phase in the reactor. By this process, an effect of suppressing foaming in the reactor is observed, whereby the reaction can be carried out under a stabilized condition. However, when the oxidation exhaust gas is recycled to the gas phase, the exhaust gas is hardly saturated in the acetic acid solvent, whereby the effect for improving the transmissivity of terephthalic acid is hardly obtainable as compared with a case where the oxidation exhaust gas is recycled to the liquid phase.

③ JP-A-7-278048 (EP 673910 A) discloses a process wherein a part of the oxidation exhaust gas is recycled in a case where a highly concentrated oxygen-containing gas which contains molecular oxygen in a concentration higher than air, is used as the gas for the oxygen source. Also by this process, the transmissivity of terephthalic acid can be improved. However, it is very disadvantageous from the viewpoint of the production cost to use a highly concentrated oxygen-containing gas. Further, as compared with the oxidation reaction employing air, the amount of the oxidation exhaust gas to be recycled has to be increased to attain the same level of the oxygen partial pressure in the gas phase in the reactor, and such is economically disadvantageous due to an increase of the power consumption or the necessity of increasing the capacity of the blower for recycling. Furthermore, since a highly concentrated oxygen-containing gas is employed, the reaction pressure in the Examples is at the same level as the reaction pressure in Comparative Example 1 where the oxidation reaction is carried out by using air without recycling the exhaust gas, whereby it is difficult to attain the effect of increasing the oxygen partial pressure in the gas phase of the reaction system as described in JP-B-5-32381.

By the above three improved processes, as is apparent from the respective Examples, an improvement in the transmissivity of terephthalic acid or in the polymerized color is observed when the oxidation reaction is carried out so that the 4CBA concentration in the resulting terephthalic acid will be constant. However, it is thereby impossible to reduce the amount of the acetic acid solvent lost by combustion or decomposition.

SUMMARY OF THE INVENTION

Under these circumstances, the present inventors have conducted various studies on a process for substantially reducing the loss of the acetic acid solvent by combustion in the production of an aromatic carboxylic acid excellent particularly in the quality and polymerized color and as a result, have found it possible to substantially reduce the combustion loss of acetic acid and to produce an aromatic carboxylic acid excellent in the quality such as transmissivity, which has been impossible to accomplish by conventional processes, by strictly selecting the combination of the catalyst composition and the reaction temperature for the oxidation reaction and further by combinating such selection with the oxidation reaction which is carried out by increasing the reaction pressure to a level higher than the pressure for a case where air is used as the molecular oxygen-containing gas and no recycling of the oxidation exhaust gas is carried out, i.e. by efficiently increasing the oxygen partial pressure in the gas phase in the reactor, by recycling a part of the oxidation exhaust gas to the liquid phase in the reactor. The present invention has been accomplished on the basis of this discovery.

That is, the present invention provides a process for producing an aromatic carboxylic acid, which comprises oxidizing an alkylaromatic hydrocarbon with a molecular oxygen-containing gas in a liquid phase in an acetic acid solvent in the presence of catalyst components comprising cobalt, manganese and bromine, wherein (1) the reaction temperature is from 140° to 180° C., (2) the cobalt component is in an amount of from 400 to 3,000 ppm by weight to the acetic acid solvent, as calculated as cobalt metal, (3) the manganese component is in an amount of from 0.001 to 0.4 time in the atomic ratio to cobalt, (4) the bromine component is in an amount of from 0.1 to 5.0 times in the atomic ratio to cobalt, (5) a part of an oxidation exhaust gas obtained by removing condensable components by condensation from a gas withdrawn from the reactor, is recycled to a liquid phase in the reactor, and (6) the reaction pressure is adjusted to a level which is higher than the pressure for a case where air is used as the molecular oxygen-containing gas and no recycling of oxidation exhaust gas is carried out.

DETAILED DESCRIPTION OF THE PREFERRED EMBODIMENTS

Figure 1:
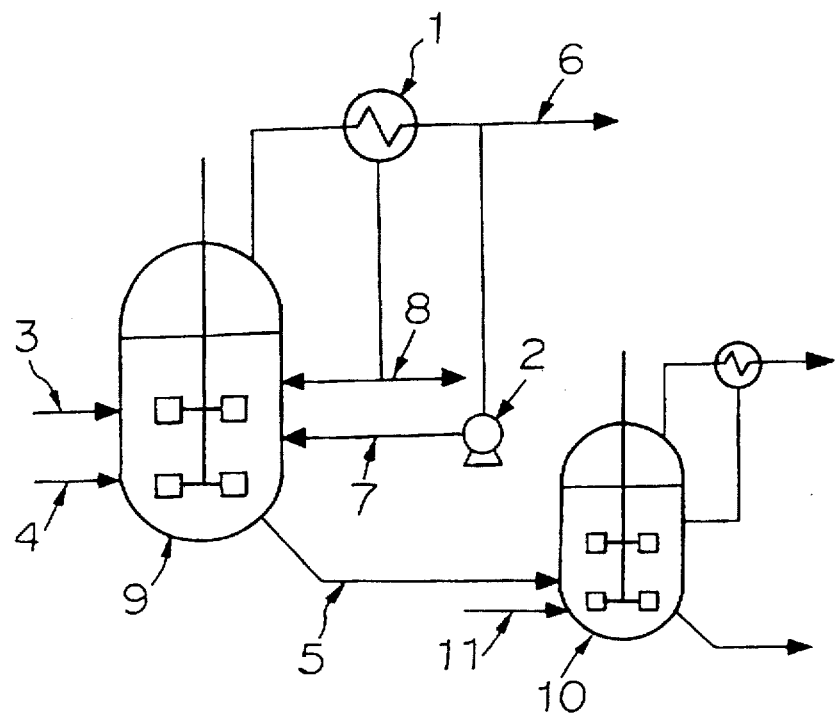
FIG. 1 illustrates the main oxidation reactor employed in the Examples of the present invention, wherein reference numeral 1 indicates a reflux condenser, numeral 2 a blower, numeral 3 a line for supplying the catalyst, the solvent and p-xylene, numeral 4 a line for introducing the oxygen-containing gas, numeral 5 a line for withdrawing the reaction slurry, numeral 6 a line for purging the oxidation exhaust gas, numeral 7 a line for recycling the oxidation exhaust gas, numeral 8 a line for withdrawing the refluxed liquid, numeral 9 a main oxidation reactor, numeral 10 an additional oxidation (second oxidation) reactor, and numeral 11 a line for introducing the oxygen-containing gas.

Now, the present invention will be described in further detail with reference to the preferred embodiments.

In the present invention, the alkylaromatic hydrocarbon used as the starting material is an aromatic hydrocarbon such as a mono-, di- or tri-alkylbenzene or a mono-, di- or tri-alkylnaphthalene, which can be converted to an aromatic carboxylic acid such as an aromatic monocarboxylic acid, an aromatic dicarboxylic acid or an aromatic tricarboxylic acid by liquid phase oxidation, and it includes the one having some alkyl groups thereof oxidized. The alkylaromatic hydrocarbon may, for example, be p-xylene, m-xylene, o-xylene, trimethylbenzene, toluene, methylnaphthalene or dimethylnaphthalene. The resulting aromatic carboxylic acid may, for example, be terephthalic acid, isophthalic acid, orthophthalic acid, trimellitic acid, benzoic acid, naphthoic acid or naphthalene dicarboxylic acid. However, the process of the present invention is preferably applied to the production of terephthalic acid or isophthalic acid, and in such a case, the alkylbenzene as the starting material may, for example, be p-xylene or m-xylene. Particularly preferred is a process for producing terephthalic acid using p-xylene as the starting material.

The acetic acid solvent is used usually in an amount of from 2 to 6 times by weight to the alkylaromatic hydrocarbon. The acetic acid solvent may contain a certain amount e.g. not more than 10 wt % of water.

As the molecular oxygen-containing gas, air, oxygen diluted with an inert gas or oxygen-rich air may, for example, be used. However, air is preferred from the viewpoint of e.g. the cost and the installation.

The catalyst is the one containing components of cobalt, manganese and bromine. With respect to specific examples of these components, the cobalt compound may, for example, be cobalt acetate, cobalt naphthenate or cobalt bromide. The manganese compound may, for example, be manganese acetate, manganese naphthenate or manganese bromide. The bromine compound may, for example, be hydrogen bromide, sodium bromide, cobalt bromide, manganese bromide or tetrabromoethane. These compounds may be used in combination.

With respect to the amount of the catalyst, the cobalt component is used usually in an amount of from 400 to 3,000 ppm by weight, preferably from 500 to 2,000 ppm by weight, to acetic acid, as calculated as cobalt metal. The manganese component is used usually in an amount of from 0.001 to 0.4 time in the atomic ratio to cobalt. Further, the absolute amount of the manganese compound is usually from 1 to 250 ppm by weight, preferably from 5 to 200 ppm by weight, to acetic acid, as calculated as manganese metal. The bromine component is used usually in an amount of from 0.1 to 5.0 times, preferably from 0.2 to 2.0 times, in the atomic ratio to cobalt. If the amount of the catalyst is outside the above ranges, the transmissivity or the purity of the resulting aromatic carboxylic acid tends to be inadequate, or combusted acetic acid tends to be substantial, whereby no adequate effects can be obtained. Especially, the amount of the manganese component is important, and if its atomic ratio to cobalt is less than 0.001 time, the reaction activities tend to substantially decrease, and if it exceeds 0.4 time, precipitation of the manganese component forms and will be included in the aromatic carboxylic acid, whereby the quality of the product deteriorates, or the loss of acetic acid increases.

Further, additional components other than the cobalt, manganese and bromine components, may be present as catalyst components. For example, a sodium component may be present usually in an amount of from 1 to 1,000 ppm, whereby an effect for preventing precipitation of the manganese component or for improving the quality, particularly the transmissivity, of the resulting aromatic carboxylic acid, may be observed. The sodium component may be added to a tank for preparation of the catalyst, or the sodium component accumulated in the system during the production process, may be utilized as it is. Further, a co-oxidizing agent may be incorporated to accelerate the reaction, as the case requires. As such a co-oxidizing agent, an aldehyde compound such as acetaldehyde, a ketone compound such as methyl ethyl ketone or an ester compound such as propyl acetate may, for example, be employed.

The oxidation reaction of the present invention is carried out under such a condition that the reaction temperature is from 140° to 180° C., preferably from 150° to 175° C. If the temperature is lower than 140° C., the reaction rate tends to be low, and if it exceeds 180° C., the loss of the acetic acid solvent by combustion tends to increase, such being undesirable. The reaction pressure is at least at a level where the mixture is maintained to be in a liquid phase at the reaction temperature and is usually from 0.2 to 5 MPa. The reaction is usually carried out continuously, and the reaction time (the average resident time) is usually from 30 to 300 minutes. The water concentration in the reaction solution is usually from 5 to 25% by weight, preferably from 7 to 20% by weight. The water concentration can be adjusted usually by withdrawing a gas evaporated in the reactor or by purging out of the system a part of a refluxed liquid of condensable components obtained by condensation of such gas.

The reactor to be used in the present invention, is usually of a type of the vessel provided with a stirrer as shown in FIG. 1. However, a stirrer is not necessarily required, the reactor may be of a bubble tower type. A reflux condenser is provided at an upper portion of the reactor, and a molecular oxygen-containing gas inlet is provided at a lower portion of the reactor. The molecular oxygen-containing gas supplied from the lower portion is, after used for the oxidation reaction, withdrawn from the reactor as a gas component accompanied by a large amount of acetic acid vapor and then after separating acetic acid by condensation by the reflux condenser, discharged as an oxidation exhaust gas. A part of the condensed liquid is purged out of the system to adjust the water content, and the rest is returned to the reactor.

To increase the oxygen partial pressure in the gas phase in the reactor as an important operational factor in the present invention, the above-mentioned process disclosed in JP-B-5-32381, i.e. the process wherein the oxidation exhaust gas obtained by removing condensable components by condensation from a gas withdrawn from the reactor, is divided into two streams, and one stream is discharged out of the system and the other stream is continuously recycled to the reactor, is employed. Further, the process wherein a part of the oxidation exhaust gas is recycled, makes it possible to adjust the reaction pressure by adjusting the amount to be recycled without giving no substantial influence over other reaction conditions. Here, it is necessary to increase the reaction pressure to a level higher than the pressure for a case where air is used as the molecular oxygen-containing gas and no recycling of the oxidation exhaust gas is carried out under the same conditions. The amount to be recycled is adjusted so that the oxygen partial pressure in the gas phase in the reactor will be usually from 1.3 to 5 times, preferably from 1.5 to 3 times, as compared with a case where air is used as the molecular oxygen-containing gas and no recycling of the oxidation exhaust gas is carried out. As the oxidation gas to be recycled, it is preferred to employ a gas having a high pressure immediately after the condensation.

The oxidation exhaust gas to be recycled, may be directly recycled to the liquid phase in the reactor from a recycling line for the oxidation exhaust gas as shown in FIG. 1, or may be mixed with the oxygen-containing gas and then supplied to the liquid phase in the reactor in the form of a gas mixture.

Further, the oxygen concentration in the oxidation exhaust gas is usually within a range of from 0.1 to 8% by volume, preferably from 0.5 to 7% by volume, in operation, since the upper limit for the oxygen concentration is usually about 8% by volume to avoid explosion.

In the present invention, a further important operational factor is that a part of the oxidation exhaust gas obtained by removing condensable components by condensing from the gas withdrawn from the reactor, is recycled to the liquid phase in the reactor, and the reaction pressure is increased to a level higher than the pressure for a case where air is used as the molecular oxygen-containing gas and no recycling of the oxidation exhaust gas is carried out under the same conditions, wherein the reaction temperature and the catalyst composition of cobalt, manganese and bromine are strictly selected, and they are combined.

In the present invention, the product may be crystallized immediately after the above oxidation reaction, or crystallization treatment may be carried out after conducting additional treatment as the case requires. As such additional treatment, a method is effective wherein the reaction mixture from the above-described first oxidation reaction (the first reaction zone) is subjected to additional oxidation (so-called post-oxidation) treatment (second oxidation treatment) in a second reaction zone maintained usually at a temperature of from 140° to 190° C. without supplying an alkylaromatic hydrocarbon. Further, a method is also effective wherein the reaction mixture from the second reaction zone is further subjected to additional oxidation (so-called post-oxidation) treatment (third oxidation treatment) in a third reaction zone usually at a temperature of at least 210° C., preferably from 220° to 280° C., without supplying an alkylaromatic hydrocarbon. The reaction mixture to be supplied for such additional oxidation (so-called post-oxidation) treatment is usually preferably such that the conversion to an aromatic carboxylic acid by the first oxidation reaction is at least 95%. The amount of the molecular oxygen-containing gas supplied to each additional oxidation (so-called post-oxidation) treatment is usually from 1/5 to 1/1,000 of the amount supplied in the first reaction, and the treating time is usually from 5 to 120 minutes.

The above additional oxidation (so-called post-oxidation) treatment is particularly effective for the aromatic carboxylic acid-containing reaction mixture obtained by the process of the present invention. The reason for this effectiveness may be such that the precipitated particles of an aromatic carboxylic acid in the reaction mixture obtained at a low reaction temperature of from 140° to 180° C. as in the present invention, have small particle sizes as compared with conventional particles of an aromatic carboxylic acid obtained under a reaction condition exceeding 180° C., or they are agglomerated particles, whereby they are susceptible to purification effects by additional oxidation (so-called post-oxidation) treatment.

Further, an aromatic carboxylic acid obtained by the process of the present invention may be treated by a conventional purification treatment such as a method wherein it is dissolved in water and contacted with a platinum group catalyst in the presence of hydrogen for purification (e.g. JP-B-41-16860).

Now, the present invention will be described in further detail with reference to Examples. However, it should be understood that the present invention is by no means restricted to such specific Examples. In the following Examples, "parts" means "parts by weight", and "ppm" means "ppm by weight".

EXAMPLE 1

A reaction was carried out by means of an apparatus for continuous reaction comprising (a) a pressure reactor 9 for main oxidation reaction made of titanium and equipped with a reflux condenser 1, a stirrer, a heater, a line 3 for supplying the catalyst, the solvent and p-xylene, a line 4 for introducing the oxygen-containing gas, a line 5 for withdrawing a reaction slurry, a line 8 for withdrawing a refluxed liquid, and a blower 2 and a recycling line 7 for recycling the oxidation exhaust gas to the reactor (see FIG. 1), (b) a pressure reactor for an additional oxidation reaction made of titanium and equipped with a reflux condenser, a stirrer, a heater, an oxygen-containing gas inlet, and an inlet and outlet for a reaction slurry, and (c) a cooling crystallizer equipped with a reflux condenser, a stirrer and an inlet and outlet for a reaction slurry.

Namely, a mixture comprising 1 part of p-xylene, 4.6 parts of acetic acid containing 5% of water, 0.0105 part of cobalt acetate tetrahydrate, 0.0003 part of manganese acetate tetrahydrate, 0.00799 part of hydrobromic acid (47% aqueous solution) and 0.0004 part of sodium hydroxide, was supplied from the line 3 of the main oxidation reactor 9 at a rate of 5.615 parts/hr (the concentrations of the respective catalyst components in the reaction system calculated from the amount of the charged catalyst, are such that cobalt (Co) is 1,100 ppm, manganese (Mn) is 33 ppm, bromine (Br) is 1,650 ppm, and sodium (Na) is 100 ppm). Further, from the line 8, the refluxed liquid was withdrawn at a rate of 1.6 parts/hr, so that the water concentration in the reaction system was adjusted to about 10%, and the oxidation reaction of p-xylene was carried out under a condition that the resident time was 100 minutes and the reaction temperature was 170° C. From the line 4, air was supplied as an oxidizing gas so that the oxygen concentration in the oxidation exhaust gas would be 6% by volume, the oxidation exhaust gas from the reflux condenser 1 was purged from line 6, and at the same time the oxidation exhaust gas was recycled to the main oxidation reactor 9 via a line 7 from the blower 2, so that the volume ratio of the recycled gas based on the non-condensable components to the oxidation exhaust gas purged out of the system would be 1.0. The reaction pressure became higher than 0.83 MPa which is the reaction pressure for a case where no recycling of the exhaust gas is carried out, and the reaction pressure was balanced at 1.10 MPa. The oxygen partial pressure in the gas phase at that time increased to 0.03 MPa from 0.015 MPa for a case where no recycling of the exhaust gas is carried out.

Then, the reaction slurry was withdrawn from the main oxidation reactor 9 via the line 5, and this slurry was continuously supplied to the additional oxidation reactor 10, and additional oxidation (so-called post-oxidation) was carried out at a reaction temperature of 176° C. under a pressure of 0.95 MPa for a resident time of 45 minutes by supplying air so that the oxygen concentration in the additional oxidation exhaust gas would be 6% by volume.

The reaction slurry after the additional oxidation (so-called post-oxidation) was then sent to the cooling crystallizer and crystallized, followed by solid-liquid separation. Then, recovered crystals were subjected to suspension washing with acetic acid and again subjected to solid-liquid separation, followed by drying to obtain TPA (terephthalic acid) crystals. Such a continuous reaction was carried out for 24 hours. Then, the transmissivity ($T_{340}$) and the 4CBA content of the obtained TPA crystals were measured, and the amount of combusted acetic acid during the production of TPA was measured. The results are shown in Table 1.

COMPARATIVE EXAMPLE 1

The reaction was carried out in the same manner as in Example 1 except that the catalyst composition was changed to 300 ppm of Co, 300 ppm of Mn and 900 ppm of Br, the reaction temperature for the main oxidation reaction was changed to 195° C., and the reaction pressure was changed to 2.07 MPa. The results are shown in Table 1. These conditions correspond to the conditions used in Examples disclosed in the above-mentioned JP-B-5-32381.

COMPARATIVE EXAMPLE 2

The reaction was carried out in the same manner as in Comparative Example 1 except that no recycling of the oxidation exhaust gas to the main oxidation reactor by the blower 2, was carried out. The results are shown in Table 1.

COMPARATIVE EXAMPLE 3

The reaction was carried out in the same manner as in Example 1 except that no recycling of the oxidation exhaust gas to the main oxidation reactor by the blower 2, was carried out. The results are shown in Table 1.

COMPARATIVE EXAMPLE 4

The reaction was carried out in the same manner as in Example 1 except that recycling of the oxidation exhaust gas to the main oxidation reactor by the blower 2 was carried out so that the oxidation exhaust gas was recycled to the gas phase in the reactor instead of the liquid phase in the reactor. The results are shown in Table 1.

COMPARATIVE EXAMPLE 5

The reaction was carried out in the same manner as in Example 1 except that the reaction temperature was changed to 195° C., and the reaction pressure was changed to 2.07 MPa. The results are shown in Table 1.

COMPARATIVE EXAMPLE 6

The reaction was carried out in the same manner as in Example 1 except that the reaction temperature was changed to 195° C., the reaction pressure was changed to 2.07 MPa, and the PX supply rate was increased so that the 4CBA concentration in the obtained terephthalic acid would be equal to that in Example 1. The results are shown in Table 1.

COMPARATIVE EXAMPLE 7

The reaction was carried out in the same manner as in Example 1 except that the catalyst composition was changed to 300 ppm of Co, 300 ppm of Mn and 900 ppm of Br, which is the catalyst composition disclosed in Examples in JP-B-5-32381 (the catalyst composition in Comparative Example 1). The results are shown in Table 1. In this Example, precipitation of the manganese component among the catalyst components was remarkable, and the reaction was unstable, so that the reaction was terminated after 2 hours from the initiation.

COMPARATIVE EXAMPLE 8

The reaction was carried out in the same manner as in Example 1 except that the catalyst composition was changed to 1,100 ppm of Co, 500 ppm of Mn and 1,650 ppm of Br. The results are shown in Table 1. In this Example, the reaction proceeded stably, but precipitation of the manganese component among the catalyst components was observed, and the transmissivity representing the quality of terephthalic acid, was poor.

TABLE 1

|  | Temp. (°C.) | Reaction Pressure (MPa) | Pressure *5 (MPa) | Oxygen partial pressure (MPa) | Amount of recycled exhaust gas *1 | Supply rate of PX (a.u.) *7 | Catalyst composition (ppm) | | | 4CBA content (ppm) | Transmissivity of terephthalic acid (%) *2 | Amount of combusted acetic acid *3 |
| --- | --- | --- | --- | --- | --- | --- | --- | --- | --- | --- | --- | --- |
|  |  |  |  |  |  |  | Co | Mn | Br |  |  |  |
| Example 1 | 170 | 1.10 | 0.83 | 0.03 | 1.0 | 1.0 | 1,100 | 33 | 1,650 | 1,500 | 80 | 0.47 |
| Comparative Example 1 | 195 | 2.07 | 1.48 | 0.06 | 1.0 | 1.0 | 300 | 300 | 900 | 1,500 | 77 | 1.00 |
| Comparative Example 2 | 195 | 1.48 | 1.48 | 0.03 | 0.0 | 1.0 | 300 | 300 | 900 | 1,500 | 64 | 1.00 |
| Comparative Example 3 | 170 | 0.83 | 0.83 | 0.015 | 0.0 | 1.0 | 1,100 | 33 | 1,650 | 5,500 | 48 | 0.51 |
| Comparative Example 4 | 170 | 0.84 | 0.83 | 0.016 | 1.0*4 | 1.0 | 1,100 | 33 | 1,650 | 5,300 | 49 | 0.53 |
| Comparative Example 5 | 195 | 2.07 | 1.48 | 0.06 | 1.0 | 0.1 | 1,100 | 33 | 1,650 | 680 | 82 | 1.53 |
| Comparative Example 6 | 195 | 2.07 | 1.48 | 0.06 | 1.0 | 1.58 | 1,100 | 33 | 1,650 | 1,500 | 78 | 1.10 |
| Comparative Example 7 | 170 | 1.10 | 0.83 | 0.03 | 1.0 | 1.0 | 300 | 300 | 900 | *6 | — | — |
| Comparative Example 8 | 170 | 1.10 | 0.83 | 0.03 | 1.0 | 1.0 | 1,100 | 500 | 1,650 | 1,000 | less than 20 | 0.87 |

The meanings of *1 to *7 in Table 1 are as follows.
*1: The amount of recycled exhaust gas indicates the volume ratio of the amount of the recycled gas based on the non-condensable components to the amount of the oxidation exhaust gas purged out of the system.
*2: The transmissivity of terephthalic acid indicates the transmissivity of a solution prepared by dissolving 7.5 g of terephthalic acid in 50 ml of a 2N potassium hydroxide aqueous solution to a light with a wavelength of 340 nm at an optical path of 10 mm in length.
*3: The amount of combusted acetic acid as a solvent is determined by analyzing the amounts of CO and $CO_2$ contained in the oxidation exhaust gas from the reactor, and calculating from these values the amount of burned acetic acid, whereupon the amount of combusted acetic acid is represented by a relative value to the amount of burned acetic acid in the method of Comparative Example 1 as the standard (1.0).
*4: The exhaust gas was recycled by the blower to the gas phase in the reactor.
*5: The pressure indicated is the reaction pressure for a case where no recycling of the oxidation exhaust gas to the reactor is carried out under the same reaction conditions as shown in each Example.
*6: The reaction was unstable, so that the reaction was terminated upon expiration of 2 hours from the initiation.
*7: The supply rate indicated is a relative value to the supply rate of p-xylene in Example 1 which is regarded to be 1.0.

Comparative Example 1 in Table 1 is an example of the reaction by the method disclosed in the above-mentioned JP-B-5-32381, i.e. the method in which the oxidation exhaust gas obtained by removing condensable components by condensation from a gas withdrawn from the reactor, was divided into two streams, and one of them was discharged out of the system and the other was continuously recycled to the liquid phase in the reactor, so that the reaction pressure was increased, and the oxygen partial pressure was increased. In Comparative Example 1, the transmissivity of terephthalic acid obtained, was good as compared with Comparative Example 2 where no recycling of the oxidation exhaust gas was carried out, but the amount of combusted acetic acid and the 4CBA content were substantially the same. These results were the same as in Examples 1 to 11 of the above-mentioned JP-B-5-32381 and in Examples 1 to 8 of the above-mentioned JP-A-7-278048. Whereas, in Example 1, the strictly selected reaction temperature and catalyst composition by the present invention were combined with the method of increasing the oxygen partial pressure by recycling the oxidation exhaust gas to the reactor, whereby not only the same effect for improving the transmissivity was observed as in Comparative Example 1, but also an effect for reducing combusted acetic acid to a large extent, was observed, which can not be accomplished by the method in Comparative Example 1.

In Comparative Example 3 wherein as opposed to Example 1, no recycling of the oxidation exhaust gas to the reactor was carried out, the reaction activities deteriorated substantially, and consequently, the 4CBA content in the obtained terephthalic acid became extremely high, and the transmissivity also deteriorated substantially, although the amount of combusted acetic acid was reduced substantially.

In Comparative Example 4, recycling of the oxidation exhaust gas to the reactor was changed so that the exhaust gas was recycled to the gas phase instead of the liquid phase, whereby the reaction results were substantially the same as in Comparative Example 3 wherein no recycling of the oxidation exhaust gas to the reactor was carried out, and no effect for improving the transmissivity was observed.

In Comparative Example 5, the reaction temperature in Example 1 was changed to 195° C., whereby the amount of combusted acetic acid increased substantially. Further, in a case where the reaction temperature in Example 1 was changed to 195° C., and the PX supply rate was increased so that the 4CBA concentration in the resulting terephthalic acid would be the same as in Example 1, no effect for reducing the amount of combusted acetic acid was observed, although the transmissivity was satisfactory.

In Comparative Examples 7 and 8 wherein the cobalt and manganese concentrations in the catalyst compositions were outside the ranges strictly selected by the present invention, the reaction activity or the quality of the obtained terephthalic acid deteriorated substantially, as compared with Example 1.

EXAMPLES 2 to 6 and COMPARATIVE EXAMPLES 9 to 11

The reactions were carried out in the same manner as in Example 1 except that the temperature for the main oxidation reaction was changed within a range of from 190° to 130° C. The reaction conditions for the catalyst concentration and the supply rate of p-xylene (PX) were selected so that the transmissivity of the resulting terephthalic acid would be substantially constant (from 75 to 81%), and the results were compared. The temperature for the additional oxidation (so-called post-oxidation) reaction was set to be the reaction temperature (from 150° to 190° C.) balanced when the pressure for the additional oxidation reaction was set at a level lower by 0.15 MPa than the pressure for the main oxidation reaction. The results are shown in Table 2.

TABLE 2

| | Temp. (°C.) | Reaction Pressure (MPa) | Pressure *5 (MPa) | Oxygen partial pressure (MPa) | Amount of recycled exhaust gas *1 | Supply rate of PX (a.u.) *7 | Catalyst composition (ppm) Co | Mn | Br | 4CBA content (ppm) | Transmissivity of terephthalic acid (%) *2 | Amount of combusted acetic acid *3 |
|---|---|---|---|---|---|---|---|---|---|---|---|---|
| Example 2 | 175 | 1.26 | 0.95 | 0.034 | 1.0 | 1.0 | 1,100 | 33 | 1,650 | 1,450 | 81 | 0.65 |
| Example 3 | 170 | 1.10 | 0.83 | 0.030 | 1.0 | 1.0 | 1,100 | 33 | 1,650 | 1,660 | 80 | 0.47 |
| Example 4 | 165 | 0.98 | 0.73 | 0.027 | 1.0 | 0.68 | 800 | 24 | 1,200 | 1,780 | 81 | 0.40 |
| Example 5 | 160 | 0.85 | 0.64 | 0.023 | 1.0 | 0.68 | 800 | 24 | 1,200 | 2,480 | 77 | 0.32 |
| Example 6 | 155 | 0.74 | 0.57 | 0.019 | 1.0 | 0.68 | 1,200 | 36 | 1,800 | 3,140 | 75 | 0.36 |
| Comparative Example 9 | 190 | 1.83 | 1.35 | 0.053 | 1.0 | 1.0 | 700 | 21 | 1,050 | 1,440 | 81 | 0.96 |
| Comparative Example 10 | 185 | 1.62 | 1.21 | 0.046 | 1.0 | 1.0 | 950 | 29 | 1,425 | 1,260 | 79 | 0.95 |
| Comparative Example 11 | 130 | — | — | — | 1.0 | 0.68 | 2,000 | 60 | 3,000 | — | *6 | — |

From Table 2, it is evident that in the temperature range shown in Examples 2 to 6, the same effect for reducing combusted acetic acid substantially, as shown in Example 1, was observed by the combination of a method of increasing the oxygen partial pressure in the gas phase in the reactor by recycling the oxidation exhaust gas to the liquid phase in the reactor, with a method of strictly selecting the reaction temperature and the catalyst composition. On the other hand, as shown in Comparative Examples 9 to 11, at a reaction temperature of 185° C. or higher, no substantial decrease in the amount of combusted acetic acid was observed, and at a reaction temperature of 130° C., the reaction activities were so low that it was impossible to conduct the operation under a stabilized condition.

According to the present invention, it is possible to substantially prevent the combustion loss of acetic acid as the solvent for reaction, while maintaining the effects of the known method for substantially improving the quality, particularly the transmittance, of an aromatic carboxylic acid obtained by an oxidation reaction. This effect is far beyond the effect disclosed or expected from the conventional inventions of the catalyst system of a similar type or from the inventions disclosed in Examples of JP-B-5-32381 or JP-A-7-278048, and is an outstanding effect which is obtainable for the first time by the combination of the specific reaction temperature condition and the specific catalyst composition with the method of increasing the oxygen partial pressure in the gas phase in the reactor by recycling the oxidation exhaust gas to the liquid phase in the reactor.

What is claimed is:

1. A process for producing an aromatic carboxylic acid, which comprises:
   oxidizing an alkylaromatic hydrocarbon with a molecular oxygen-containing gas in a liquid phase in an acetic acid solvent in the presence of catalyst components comprising cobalt, manganese and bromine, wherein:
   (1) the reaction temperature ranges from 140°–180° C.,
   (2) the cobalt component is present in an amount of from 400–3,000 ppm by weight to the acetic acid solvent, calculated as cobalt metal,
   (3) the manganese component is present in an amount such that the Mn/Co atomic ratio ranges from 0.001–0.4,
   (4) the bromine component is present in an amount such that the Br/Co atomic ratio ranges from 0.1–5.4,
   (5) a portion of an oxidation exhaust gas obtained by removing condensable components by condensation from a gas withdrawn from the reactor, is recycled to the liquid phase in the reactor, and
   (6) the reaction pressure is adjusted to a level which is higher than the pressure in the case where air is used as the molecular oxygen-containing gas and no recycling of the oxidation exhaust gas is conducted.

2. The process for producing an aromatic carboxylic acid according to claim 1, wherein the alkylaromatic hydrocarbon is p-xylene.

3. The process for producing an aromatic carboxylic acid according to claim 1, wherein the cobalt component is present in an amount of from 500 to 2,000 ppm by weight to the acetic acid solvent, calculated as cobalt metal.

4. The process for producing an aromatic carboxylic acid according to claim 1, wherein the manganese component is present in an amount of from 1 to 250 ppm by weight to the acetic acid solvent, calculated as manganese metal.

5. The process for producing an aromatic carboxylic acid according to claim 1, wherein the reaction temperature ranges from 150° to 175° C.

6. The process for producing an aromatic carboxylic acid according to claim 1, wherein the oxygen concentration in the oxidation exhaust gas ranges from 0.1 to 8% by volume.

7. The process for producing an aromatic carboxylic acid according to claim 1, wherein the oxygen partial pressure in the gas phase in the reactor is adjusted so that it ranges from 1.3 to 5 times the oxygen partial pressure in the event air is used as the molecular oxygen-containing gas and no recycling of the oxidation exhaust gas is carried out.

8. The process for producing an aromatic carboxylic acid according to claim 1, wherein the molecular oxygen-containing gas supplied to the oxidation reaction is air.

9. The process for producing an aromatic carboxylic acid according to claim 1, wherein a sodium component is present as a catalyst component in an amount of from 1 to 1,000 ppm by weight to the acetic acid solvent, calculated as sodium metal.

10. The process for producing an aromatic carboxylic acid according to claim 1, wherein the oxidation reaction is carried out in the absence of a co-oxidizing agent which accelerates the reaction.

11. A process for producing an aromatic carboxylic acid, wherein the reaction mixture obtained by the process of claim 1 is subjected to a second oxidation treatment with a molecular oxygen-containing gas in a second reaction zone maintained at a temperature of from 140° to 190° C. without supplying an alkylaromatic hydrocarbon to the reaction medium.

12. A process for producing an aromatic carboxylic acid, wherein the reaction mixture obtained by the process of claim 11 is subjected to a third oxidation treatment with a molecular oxygen-containing gas in a third reaction zone maintained at a temperature of at least 210° C. without supplying an alkylaromatic hydrocarbon to the reaction medium.

13. The process for producing an aromatic carboxylic acid according to claim 1, wherein the bromine component is present in an amount such that the Br/Co atomic ratio ranges from 0.2–2.0.

14. The process for producing an aromatic carboxylic acid according to claim 1, wherein the manganese component is present in an amount ranging from 5–200 ppm by weight.

15. The process for producing an aromatic carboxylic acid according to claim 1, wherein the water concentration in the reaction solution ranges from 5–25% by weight.

16. The process for producing an aromatic carboxylic acid according to claim 1, wherein the cobalt component is cobalt acetate, cobalt bromide or cobalt naphthenate.

17. The process for producing an aromatic carboxylic acid according to claim 1, wherein said manganese component is manganese acetate, manganese bromide or manganese naphthenate.

18. The process for producing an aromatic carboxylic acid according to claim 1, wherein the bromine component is hydrogen bromide, sodium bromide, cobalt bromide, manganese bromide or tetrabromoethane.

* * * * *

UNITED STATES PATENT AND TRADEMARK OFFICE
CERTIFICATE OF CORRECTION

PATENT NO. : 5,763,648
DATED : June 9, 1998
INVENTOR(S) : Hashizume, et al

It is certified that error appears in the above-identified patent and that said Letters Patent is hereby corrected as shown below:

Column 12, line 6, delete "5.4" and insert -- 5.0 --.

Signed and Sealed this

Sixteenth Day of March, 1999

Attest:

Q. TODD DICKINSON

Attesting Officer

Acting Commissioner of Patents and Trademarks